United States Patent [19]

Eidenschink et al.

[11] Patent Number: 4,833,035

[45] Date of Patent: May 23, 1989

[54] ORIENTED POLYMER MATERIALS

[75] Inventors: Rudolf Eidenschink, Mühltal; Dieter Dorsch, Darmstadt; Claus P. Herz, Heidelberg, all of Fed. Rep. of Germany

[73] Assignee: Merck Patent Gesellschaft Mit Beschränkter Haftung, Darmstadt, Fed. Rep. of Germany

[21] Appl. No.: 76,819

[22] Filed: Jul. 23, 1987

[30] Foreign Application Priority Data

Jul. 23, 1986 [DE] Fed. Rep. of Germany ....... 3624858

[51] Int. Cl.$^4$ ............................ B32B 9/04; B05D 5/06
[52] U.S. Cl. ................................. 428/411.1; 427/162; 427/163
[58] Field of Search ..................... 428/411.1, 520, 521, 428/480; 427/162, 163; 528/192

[56] References Cited

U.S. PATENT DOCUMENTS 4,412,059 10/1983 Krigbaum et al. .................. 528/192
4,536,450  8/1985 Garito ............................ 428/521 X

FOREIGN PATENT DOCUMENTS 0021695  1/1981 European Pat. Off. ......... 428/411.1

OTHER PUBLICATIONS

McGraw-Hill Concise Encyclopedia of Science & Technology, pp. 1161-1162.
Dictionary of Scientific and Technical Terms, McGraw-Hill Book Co., 1976, p. 1011.

Primary Examiner—Thomas J. Herbert
Attorney, Agent, or Firm—Millen & White

[57] ABSTRACT

Vertically oriented polymer materials with nonlinear optical properties are obtained by polymerization of monomers containing polar groups.

7 Claims, No Drawings

ORIENTED POLYMER MATERIALS

BACKGROUND OF THE INVENTION

The invention relates to new polymer materials with non-linear optical properties and processes for their preparation.

Non-linear optics are concerned with the interaction of electromagnetic fields in various media and the associated formation of new fields with changed properties. Materials with non-linear optical properties have a dielectric susceptibility which depends on the field strength and results in a number of dispersive processes: frequency doubling (second harmonic generation=SHG) allows generation of light of half the wavelength compared with the incident light; the electrooptical effect (Pockels effect) allows a change in the refractive index when a direct current electrical field is applied; methods of sum and difference frequency mixing and frequency distribution permit continuous adjustment of laser light.

The abovementioned effects result in a large number of technical applications. Optical switches and waveguides for construction of purely optical computers, frequency and intensity control in laser technology, holography and the sectors of information processing and integrated optics are exemplary fields of use for materials with non-linear optical properties.

In order to be suitable for use in the field of non-linear optics, such materials must fulfill a number of requirements. One such requirement is that arrangement of the molecules in crystalline form should be non-centrosymmetric. In addition, technical usefulness requires that the materials have the maximum possible values for dielectric susceptibility, $\chi$(Y. R. Shen, The Principles of Nonlineaar Optics, Chapter VI, John Wiley, New York, 1985).

A number of inorganic substances, such as, for example, potassium dihydrogen phosphate or lithium niobate, exhibit non-linear optical properties. However, all these compounds have diverse disadvantages. As well as inadequate values of the second order dielectric susceptibility, inorganic compounds frequently have the deficiency of inadequate photostability during treatment with high light intensities or, as a result of being highly colored, inadequate transparency.

Organic compounds of the nitroaniline type are known from Garito et al., Laser Focus 18 (1982) and European Pat. No. 0,091,838. Their relatively good values for photochemical stability and second order dielectric susceptibility are accompanied, however, by a poor crystallizability and a lack of mechanical stability. In particular, it is not possible to prepare thin layers, as required by integrated optics, with these materials.

Polymers are distinguished by a high mechanical resistance and good chemical stability. Molecules with non-linear optical properties attached to the polymer skeleton or dissolved in the polymer should therefore have high mechanical resistance and good chemical stability combined with advantageous values of dielectric susceptibility in the non-centrosymmetric environment.

Polymers with second order non-linearities can be prepared by applying an external field to polymer films heated above the glass transition temperature and doped with randomly oriented molecules. This leads to poling of the embedded molecules which imparts anisotropy to the polymer medium after the medium has solidified. Polymers which are prepared in this manner, have non-linear optical properties. Such doped polymer systems wherein p,p'-dimethylamino-nitrostilbene is used as the host molecule have been described by Meredith et al., Macromolecules 15 (1982) 1385.

Shibaev et al., Polymer Communications 24 (1983) 364 report field-induced alignment of liquid crystal polymers with mesogenic side groups.

U.S. Pat. No. 4,412,059 discloses a polymer material with cholesteric mesophases which are accessible by means of electric or magnetic fields with a controlled alignment. In addition, fully aromatic, thermotropic, liquid crystal polymers in which the non-linear optical properties can likewise be caused by external fields are known from European Pat. No. 0,172,012.

Another method for producing polymer materials with non-linear optical properties comprises polymerization of already ordered monomers with a non-centrosymmetric orientation, the order of this system largely being retained during the polymerization. Monomers which are suitable for this technique are to be found, for example, in European Pat. No. 0,021,695.

The materials obtained by the processes described above still have unsatisfactory non-linear optical properties. Only incomplete alignment of the composite polymer is obtained by the action of an external field, which is an additional process step. In the pre-ordered monomers incomplete alignment results from orientation losses occurring during polymerization.

SUMMARY OF THE INVENTION

It is an object of this invention to provide oriented polymer materials applied to a surface, and a process for their preparation, wherein the polymer materials do not possess the disadvantages described above, or display them to only a slight degree.

It is a further object of the invention to provide a process for the preparation of oriented polymer materials which in particular allows the polymer structure already to be oriented during the polymerization operation without the need for additional process steps.

Upon further study of the specification and appended claims, further objects and advantages of this invention will become apparent to those skilled in the art.

The objects are achieved by a process according to the invention wherein polymer materials containing monomer units with polar groups are attached to a substrate by subjecting cyclic monomers to ring-opening polymerization using initiators anchored to the substrate or by first polymerizing monomer units and attaching the resultant polymers to the substrate.

The invention therefore relates to polymer materials comprising polar monomer units applied to a surface characterized in that the monomer units and the main polymer chains have an orientation which is preferably perpendicular to the substrate surface. In a particularly preferred group of polymer materials according to the invention, the monomer units are preferably aligned in dipolar arrangement. The degree of perpendicular orientation is preferably at least about 60% for both monomers and polymer chains with an angular deviation from the perpendicular of not more than about 10°, and especially at least about 80% with an angular deviation of not more than about 5°.

The invention furthermore relates to a process for the preparation of such polymer materials by a procedure in which cyclic monomers which contain polar groups and are capable of ring-opening polymerization are polymerized in the presence of a polymerization initiator anchored on the substrate surface, or by a procedure in which monomers containing polar groups are polymerized and then anchored onto a substrate surface.

Polymer materials obtained by this process are suitable as optically non-linear media.

Ring-opening polymerization of cyclic monomers is known. Thus, processes for ionic ring-opening and subsequent polymerization of, for example, ethylene oxide, tetrahydrofuran, caprolactone and caprolactam are described in Frisch, Reegen (editors), Ring-opening Polymerization, Marcel Dekker, New York, 1969, Saegusa, Goethals (editors), Radical Polymerization American Chemical Society, Washington, 1977 and Yvin, Saegusa (editors), Ring-Opening Polymerization, Elsevier, London, 1984.

Monomers which are accessible to free radical ring-opening and polymerization are, for example, bicyclobutanes (Hall, Ykman, J. Macromol, Sci, Rev. Macromol. Chem. 11 (1976)), Olefins (Errede, J. Polym. Sci., 49 (1961) 253), spiroorthocarbonates (Endo, Bailey, J. Polym. Sci., Polym. Lett. Ed. 18 (1980) 25) or cyclic ketene acetals (Endo et al., Makromol. Chem. 186 (1985) 1543); the free radicals can be formed by heat or photochemically.

It has now been found, surprisingly, that ring-opening polymerization of cyclic monomers containing polar groups, of the general formula I

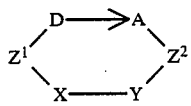

I wherein
D→A is a molecular fragment comprising an organic skeleton containing polar groups D and A,
$Z^1$ and $Z^2$ are unsubstituted or substituted carbon chains, in which one or more C atoms are optionally replaced by hetero atoms, and
X—Y is a group which can be split to form a monomer fragment capable of polymerization in the presence of a polymerization initiator anchored to a substrate surface, gives novel polymer materials. The monomer units and main polymer chains preferably have a perpendicular orientation towards the substrate surface. Such polymer materials are outstandingly suitable as non-linear optical media.

In the cyclic monomers of the formula I to be polymerized, the polar group D in the molecular fragment D→A has the properties of an electron donor group, such as, for example, an amino, ether, phosphine or alcohol group, while polar group A has the properties of an electron acceptor group, such as, for example, a nitro, cyano, ester or anhydride group, or a quinone or halogen. Preferably, D denotes an amino or alcohol group and A denotes a nitro or ester group. (D. J. Williams, Angew. Chem., Int. Ed. Engl. 23, 690 (1984)).

The above mentioned groups are located on an organic skeleton, preferably an aromatic system. Systems which are suitable here are, for example, benzene which is substituted by the groups D and A in the 1,2- or 1,4-position, biphenyl or stilbene which is substituted by groups D and A in the 4,4'-position or naphthalene which is substituted by groups D and A in the 2,6-position.

$Z^1$ and $Z^2$ each independently represent an alkyl chain having 1 to 18 C atoms, in which one or more $CH_2$ groups can also be replaced by —O—, —CO—, —CO—O—, —NH—, —N(alkyl)— or —CH=CH—. Preferred replacing groups are —O—, —CO—O— and —NH—.

The group X—Y which can be split to produce fragments capable of polymerization is a structural element which can be split by free radicals, ionically or heat, such as, for example, peroxides (X—Y=O—O), cyclic orthoesters (O—CHR—O; R=organic radical), cyclic orthocarbonates (O—C(OR)$_2$—O) or ketene acetals (O—C(=CR$_2$)—O), the latter being a preferred group X—Y.

Cyclic monomers with these reactive groups are obtainable in accordance with instructions which can be found in the above-mentioned publications or by methods which are known per se, such as are described in the literature (for example in the standard works, such as Houben-Weyl, Methoden der Organischen Chemie (Methods of Organic Chemistry), Georg-Thieme-Verlag, Stuttgart), and in particular under reaction conditions which are known and suitable for the reactions mentioned. Variants which are known per se and are not mentioned in more detail can also thereby be used.

Thus, for example, the particular preferred monomers of the formula I in which X—Y denotes a ketene acetal function are obtainable from 2-halogenomethyl-1,3-dioxacyclo compounds by the action of a strong base, such as, for example, sodium amide or potassium tert.-butanolate, in an inert solvent.

The precise structure of the monomer is uncritical as long as the molecular structure provides a substrate for the two polar groups D and A and a means for polymerizing the substrate such that the necessary recurring structure described herein is achieved, preferably via the X—Y moiety. In essence, any polymer will be appropriate for use in accordance with this invention as long as its recurring unit has the dipolar moiety D→A.

The specific nature of the groups to which D and A are attached is non-critical as are the details of the Z chains and the identity of the R groups which may also include H.

The photoinitiators required to start the polymerization are anchored to the substrate in a suitable manner. Adhesion to the particular substrate can be achieved on the basis of physical, for example adsorptive, or chemical interactions. Physically adhering photoinitiators can be applied to the substrate, for example, by coating, printing, vapor-depositing or immersion. After removal of excess non-adhering photoinitiator, the substrates thus coated can be provided with a polymerizable monomer coating directly, for use in the process according to the invention.

A large number of known initiators, such as are described for example, in Pappas (editor), UV Curing: Science and Technology, Technology Marketing Corp., Stamford, CT, 1978, or in Ocian, Principles of Polymerization, McGraw-Hill, New York, are suitable for starting the polymerization. Examples of free radical initiators which dissociate under the influence of heat are percompounds, such as potassium persulfate, dibenzoyl peroxide and cyclohexanone peroxide, and examples of initiators which dissociate by the action of radiation are benzophenones, such as, for example, Michler's ketone [4,4'-bis(dimethylamino)benzophenone], 4,4'- bis(diethylamino)-benzophenone, p-dimethylaminobenzophenone, p-chlorobenzophenone and benzophenone; anthraquinones, such as, for example, anthraquinone, 2-chloroanthraquinone and 2-alkylanthraquinones; xanthones, such as, for example, 2-halogenoxanthones or 2-alkylxanthones; thioxanthones, such as 2-chlorothioxanthone and 2-alkylthioxanthones; acridanones, such as, for example, 2-alkylacridanones or N-substituted acridanones; benzoins, such as, for example, p-dimethylaminobenzoin and alkyl ethers of benzoin; benzil ketals, α-halogenoketones, dialkoxyacetophenones, α-hydroxyalkylphenones and α-aminoalkylphenones, such as are described, for example, in German Offenlegungsschrift No. 2,722,264 and in European Published Application 3,003, and furthermore, for example, fluorenones, dibenzosuberones, phenanthrenequinones, benzoic acid ethers, such as, for example, hydroxypropyl benzoate and benzoylbenzoate acrylate, as well as onium salts, such as, for example, diaryliodonium or triarylsulfonium salts.

Examples of ionic catalysts useful for free radical polymerization are hydroxides, such as potassium hydroxide, alkali metal-organic compounds, such as phenyllithium and naphthalenesodium, Lewis acids, such as $BF_3$, $AlCl_3$, $SnCl_4$ and $TiCl_4$, metal complexes in the form of aluminum or titanium compounds and strong acids, such as fluorosulfonic acid.

Photoinitiators which adhere chemically to the substrate surface are bonded to reactive groups of the substrate material via a chemical bond.

A particularly preferred method for fixing photoinitiators onto a surface containing hydroxy functional groups comprises reacting the photoinitiators with difunctional silanes of the general formula II $$X_3Si\text{—}Z\text{—}Ar\text{—}CO\text{—}C(OR^1)R^2R^3 \qquad II$$

wherein
Ar is an optionally substituted aryl radical;
$R^1$ is H, alkyl or alkanoyl;
$R^2$ and $R^3$ are each independently H, alkyl or aryl, or $R^2$ and $R^3$ together are alkylene, and one of the radicals $R^2$ or $R^3$ can also be $OR^1$;
X is a functional group which is capable of reacting with the substrate surface and
Z is an alkylene group in which one or more $CH_2$ groups can be replaced by hetero atoms.

Preferably, Ar is 1,4-phenylene, $R^1$ is H or, if one of the radicals $R^2$ or $R^3$ is $OR^1$, R is preferably alkyl. $R^2$ and $R^3$ are preferably alkyl or together are alkylene and X is halogen, alkoxy or alkanoyloxy.

Methods such as are known, for example, from Deschler et al., Angew. Chem. 98 (1986) 237 or from German Pat. No. 3,521,201 can be used to prepare the photoinitiators containing reactive silane groups. It is also possible for variants which are known per se but are not mentioned in more detail here thereby to be used. The functionalized photoinitiators are advantageously applied by means of coating, printing or immersion techniques. After-treatment with heat, if appropriate with simultaneous charging with a steam atmosphere, of the coated substrate may sometimes be appropriate for bringing the reaction to completion and/or shortening the duration of the reaction.

The cyclic monomers to be polymerized are applied to the substrate surfaces coated with an initiator layer to a desired coating thickness in the manner described above for application of the initiator layer. The cyclic monomers are polymerized by supplying thermal energy or by irradiation.

Thermal polymerization is carried out, for example, by simple heating, by treatment through the means of ultrasound or microwaves or by the action of IR radiation.

Photopolymerization is carried out by methods which are known per se by irradiation with light or UV radiation of the wavelength range from 250 to 500 nm, preferably 300 to 400 nm. Sunlight or artificial lamps can be used as radiation sources. Examples of advantageous lamps are high pressure, medium pressure or low pressure mercury lamps, xenon lamps and tungsten lamps; laser light sources can also be used.

In another process for the preparation of the vertically oriented polymer materials according to the invention, monomers containing polar groups are polymerized and the polymers are then anchored onto a substrate surface.

Suitable monomers are reacted by the customary methods of polymerization, polycondensation and/or polyaddition to give polar homopolymers or copolymers of the general formula III $$H\text{—}(Z^1\text{—}D\rightarrow A\text{—}Z^2\text{—})_n V \qquad III$$

in which $D\rightarrow A$ and $Z^1$ and $Z^2$ have the meaning given in the case of formula I, n is an integer which expresses the degree of polymerization and V is a functional group which is suitable after modification, if appropriate, for anchoring to the substrate.

Preferably, $D\rightarrow A$ and $Z^1$ and $Z^2$ have the meaning given in for formula I; n is preferably 10–1000, in particular 20–100, and V is preferably $\text{—}NH_2$, $\text{—}OH$ or $\text{—}SH$, in particular $\text{—}OH$.

A particularly preferred group of polymers of the formula III is the polyesters. Methods for their preparation can be found, for example, in Jin et al., Br. Polym. J. 12 (1980) 132 and Preston, Ang. Makromol. Chem. 109/110 (1982) 1.

The functionalization of the polyesters by means of reactive silanes can be carried out in accordance with the method of Deschler, loc. cit., or by other methods known from the literature, for example described in Houben-Weyl, Methoden der Organischen Chemie (Methods of Organic Chemistry), Georg-Thieme-Verlag, Stuttgart, volume 13/5.

On application of these polyesters containing silicon functional groups to suitable substrates by, for example, coating, immersion or printing techniques, chemical bonding to the substrate surface takes place. After excess unreacted polyester has been removed, a polymer layer which adheres firmly to the surface and in which the polar monomer units and main polymer chains are preferably oriented perpendicularly is obtained. The thickness of the coating can be varied within wide limits, and therefore adjusted to suit the particular intended use, by changing the degree of polymerization of the polymers employed.

Polymer materials prepared in this way exhibit the vary same advantageous non-linear optical properties as those materials described above obtained by polymerization on cyclic monomers containing polar groups in the presence of a polymerization initiator anchored to the substrate surface.

Because of their advantageous non-linear optical properties, the polymer materials according to the invention open up a wide field of use. In particular, they are suitable for frequency doubling of laser light and for the production of switching elements, waveguides and phase modulators in the field of integrated optics.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLE 1

(a) A solution of 26.6 g of 4'-(6-hydroxyhexyloxy)-(1,1')-biphenyl-4-carboxylic acid, 16 g of epoxystyrene and 16 g of triethylamine in 300 ml of tetrahydrofuran is heated at the boiling point for 140 hours. It is diluted with 1000 ml of methylene chloride, washed twice with 2N hydrochloric acid and dried over sodium sulfate. After concentration under reduced pressure, the residue is crystallized from ethanol. 2-Hydroxy-2-phenylethyl 4'-(6-hydroxyhexyloxy)-1,1')-biphenyl-4-carboxylate is obtained; melting point: 148°–150°.

(b) A mixture of 6.1 g of 2-hydroxy-2-phenylethyl 4'-(6-hydroxyhexyloxy)-(1,1')-biphenyl-carboxylate, 4.4 g of chloroacetaldehyde dimethylacetal and 3 mg of p-toluenesulfonic acid is kept at a temperature of 140° for 2 days. Methanol formed during the reaction is thereby distilled off continuously. After drying under reduced pressure, the cyclic acetal 9-chloromethyl-14-oxo-11-phenyl-1,8,10,13-tetraoxa[14](4,4')-biphenylophane is obtained as a viscous oil.

(c) A solution of 1.98 g of 9-chloromethyl-14-oxo-11-phenyl-1,8,10,13-tetraoxa[14](4,4')-biphenylophane, 532 mg of potassium tert.-butanolate and 8 ml of tert.-butanol is heated at 80° for 24 hours. After addition of 12 ml of petroleum ether, the potassium chloride which has precipitated is filtered off over a membrane filter. The filtrate is concentrated and dried under reduced pressure. 9-Methylene-14-oxo-11-phenyl-1,8,10,13-tetraoxa[14](4,4')-biphenylophane remains as a viscous colorless oil.

(d) 0.1 ml of a 0.02M solution of tetrachloroplatinic-(II) acid hexahydrate in 2-propanol is added to a solution of 5.05 g of allylbenzoin and 6.57 g of triethoxysilane and the mixture is then heated at the boiling point for 70 hours. It is concentrated and dried under reduced pressure for 16 hours, after which α-(3-triethoxysilyl-propyl)-benzoin remains as a colorless oil.

The following compounds are obtained analogously:
2-hydroxy-2-methyl-1-(4-(3-triethoxysilyl-propyloxy)-phenyl)-propan-1-one
2-hydroxy-2-methyl-1-(4-(2-(3-triethoxysilyl-propyloxy)-ethoxy)-phenyl)-propan-1-one

EXAMPLE 2

A 1% solution of α-(3-triethoxysilyl-propyl)-benzoin in ethanol is applied to a glass substrate by immersion. Thereafter, the substrate is dried at 180° for 10 minutes and the surface is then rinsed with isopropanol.

The glass substrate coated with initiator is immersed in a 10% solution of the cyclic ketene acetal 9-methylene-14-oxo-11-phenyl-1,8,10,13-tetraoxa[14](4,4')-biphenylophane from Example 1c and provided with an approximately 3 μm thick layer of this monomer. For polymerization, the substrate is irradiated with a mercury vapor lamp for 5 minutes. After removal of unreacted monomers by rinsing with tetrahydrofuran, a colorless, firmly adhering polymer layer which has a high degree of perpendicular orientation of the monomer units and main polymer chains and a very good frequency doubling capacity is obtained.

EXAMPLE 3

(a) A mixture of 629 mg of 4'-(6-hydroxyhexyloxy)-(1,1')-biphenyl-4-carboxylic acid, 144 mg of 6-(6-hydroxyhexyloxy)-naphthalene-2-carboxylic acid and 4 mg of p-toluenesulfonic acid is heated at 215° under a pressure of 10 mm Hg for 4 hours and then at 230° under a pressure of 0.1 mm Hg for 1 hour. The copolymer formed has a vitreous nature and nematic liquid crystal properties (clear point 200°), with an average molecular weight of about 14,000.

The corresponding homopolymer is obtained analogously from 4'-(6-hydroxyhexyloxy)-(1,1')-biphenyl-4-carboxylic acid; crystalline, melting point 235°.

(b) 50 μl of octanol are added to 140 mg of the copolymer obtainable in the manner described above and the mixture is heated at 210° for 3 hours and then freed from volatile portions at the same temperature under a pressure of 10 mm Hg.

The residue is dissolved in 3 ml of N-methylpyrrolidone and 150 μl of tetrachlorosilane are added. Thereafter, the reaction mixture is charged with a pressure of 10 mm Hg for a short time.

The resulting solution of the polyester containing silane functional groups is applied to a glass substrate by immersion. After heating at 210° for 20 minutes, a firmly adhering polymer film has formed, in which the main polymer chains and monomer units are oriented to a high degree perpendicularly to the substrate surface and which has marked non-linear optical properties.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In an article comprising a substrate coated on its surface with a polymer containing polar monomer units, the improvement wherein said monomer units and the main polymer chains of the polymer have a substantially perpendicular orientation with respect to the surface.

2. An article of claim 1, wherein at least about 60% of the monomer units and 60% of the main polymer chains have an orientation with respect to the surface which does not deviate from the perpendicular by more than about 10°.

3. An article of claim 1, wherein said monomer units have a dipolar alignment.

4. An article according to claim 1, wherein said polar monomer units possess an electron donor polar group and an electron acceptor polar group.

5. A process for the preparation of an article according to claim 1, comprising polymerizing cyclic monomers capable of ring-opening polymerization and possessing polar groups in the presence of a polymerization initiator anchored to the substrate surface whereby the main polymer chain of the resultant polymer have a substantially perpendicular orientation with respect to the substrate surface.

6. A process for the preparation of an article according to claim 1, comprising polymerizing monomers possessing polar groups and then anchoring the resultant polymer to the substrate surface whereby the main polymer chain of the resultant polymer have a substantially perpendicular orientation with respect to the substrate surface.

7. In a method for achieving a non-linear optical effect by impinging light on a surface, the improvement comprising impinging light on a coated surface according to claim 1.

* * * * *